(12) United States Patent
Grassauer et al.

(10) Patent No.: US 10,022,449 B2
(45) Date of Patent: Jul. 17, 2018

(54) SYNERGISTIC ANTIVIRAL COMPOSITION AND USE THEREOF

(75) Inventors: Andreas Grassauer, Vienna (AT); Eva Prieschl-Grassauer, Vienna (AT); Christiane Meier, Seyring/Gerasdorf (AT); Marielle Konig-Schuster, Vienna (AT)

(73) Assignee: MARINOMED BIOTECHNOLOGIE GmbH, Vienna (AT)

( * ) Notice: Subject to any disclaimer, the term of this patent is extended or adjusted under 35 U.S.C. 154(b) by 0 days.

(21) Appl. No.: 13/513,961

(22) PCT Filed: Dec. 17, 2010

(86) PCT No.: PCT/EP2010/007726
§ 371 (c)(1),
(2), (4) Date: Jun. 5, 2012

(87) PCT Pub. No.: WO2011/076367
PCT Pub. Date: Jun. 30, 2011

(65) Prior Publication Data
US 2012/0302522 A1   Nov. 29, 2012

Related U.S. Application Data

(60) Provisional application No. 61/282,148, filed on Dec. 22, 2009.

(51) Int. Cl.
| | | |
|---|---|---|
| *A61K 31/731* | (2006.01) | |
| *A61K 31/715* | (2006.01) | |
| *A61P 31/12* | (2006.01) | |
| *A61K 47/36* | (2006.01) | |
| *A61K 31/13* | (2006.01) | |
| *A61K 31/19* | (2006.01) | |
| *A61K 45/06* | (2006.01) | |

(52) U.S. Cl.
CPC ............... *A61K 47/36* (2013.01); *A61K 31/13* (2013.01); *A61K 31/19* (2013.01); *A61K 31/731* (2013.01); *A61K 45/06* (2013.01)

(58) Field of Classification Search
CPC ...... A61K 31/13; A61K 31/19; A61K 31/731; A61K 45/06; A61K 47/36; A61K 2300/00
USPC .................... 514/54, 23; 536/123.1
See application file for complete search history.

(56) References Cited

U.S. PATENT DOCUMENTS 6,593,314 B1 *   7/2003   Maring et al. ............... 514/151

FOREIGN PATENT DOCUMENTS

| EP | 1930015 A1 * | 6/2008 |
|---|---|---|
| WO | WO 2008/067982 A2 | 6/2008 |
| WO | WO 2008/147468 A2 | 12/2008 |
| WO | WO 2009/027057 A1 | 3/2009 |

OTHER PUBLICATIONS

Lin et al. (Current Medical Research and Opinion (2006), 22(1), 75-82).*
Hayden (Vaccine 19 (2001) S66-S70).*
Lehar J, et al. "Synergistic drug combinations tend to improve therapeutically relevant selectivity." Nat Biotechnol 27: 659-666, (2009).*
Garcia-Sosa et al., "Design of Multi-Binding-Site Inhibitors, Ligand Efficiency, and Consensus Screening of Avian Influenza H5N1 Wild-Type Neuraminidase and of the Oseltamivir-Resistant H274Y Variant," *J. Chem. Inf. Model*, vol. 48, pp. 2074-2080, Nov. 10, 2008.
Burch et al., "Prescription of anti-influenza drugs for healthy adults: a systematic review and meta-analysis," *Review*, vol. 9, pp. 537-545, Sep. 2009.
Ludwig, S., "Targeting cell signaling pathways to fight the flu: towards a paradigm change in anti-influenza therapy," *Journal of Antimicrobial Chemotherapy*, vol. 64, pp. 1-4, 2009.
Written Opinion of the International Search Authority issued in Application No. PCT/EP2010/007726; dated Jun. 17, 2011.
International Search Report issued in Application No. PCT/EP2010/007726; dated Jun. 17, 2011.
Hayashi et al., "Promising Antiviral Glyco-Molecules from and Edible Alga," *Combating the Threat of Pandemic Influenza: Drug Discovery Approaches*, 2007, pp. 166-182.
Toshimitsu Hayashi, "Studies on Earth of Natural Products for Antiviral Effects and Their Applications," The Pharmaceutical Society of Japan, 2008, pp. 61-79 (with English abstract).

* cited by examiner

*Primary Examiner* — Shaojia Anna Jiang
*Assistant Examiner* — Michael C Henry
(74) *Attorney, Agent, or Firm* — Oliff PLC

(57) ABSTRACT

The present invention relates to iota- and/or kappa-carrageenan in combination with a neuraminidase inhibitor for use as a medicament in the prophylactic or therapeutic treatment of a symptom, condition or disease caused by or associated with an infection by an influenza virus.

7 Claims, 2 Drawing Sheets

SYNERGISTIC ANTIVIRAL COMPOSITION AND USE THEREOF

FIELD OF THE INVENTION

Figure 1:
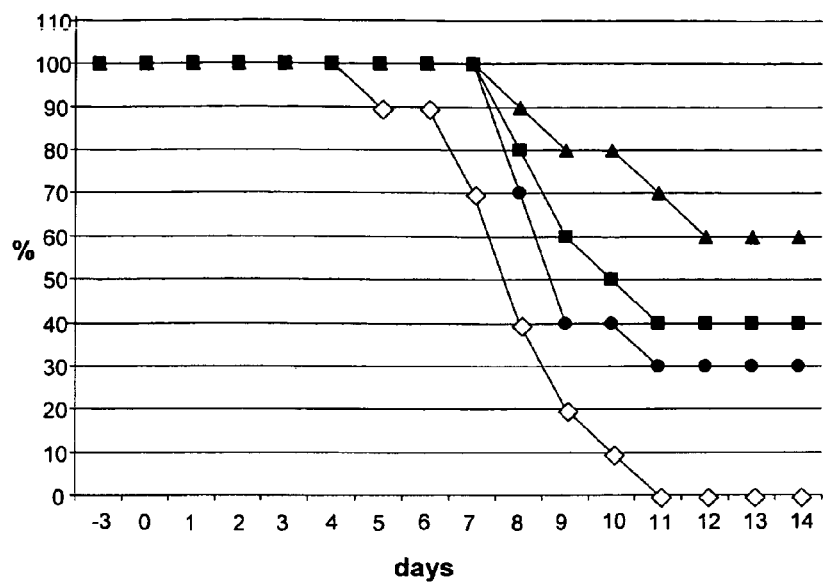

The present invention is in the field of immunology and relates to the use of carrageenan in combination with a neuraminidase inhibitor for the prophylactic or therapeutic treatment of influenza virus infection.

STATE OF THE ART

Structurally, the carrageenans are a complex group of polysaccharides made up of repeating galactose-related monomer units. Currently, three main types of carrageenan are distinguished, namely lambda, kappa, and iota carrageenan.

The antiviral effect of iota- and kappa-carrageenan against orthomyxoviridae, paramyxoviridae and coronaviridae has been previously disclosed in WO2009/027057. The antiviral effect of iota- and kappa-carrageenan against a rhinovirus infection has been previously disclosed in WO2008/067982. These polymers have been shown to be useful in the preparation of antiviral pharmaceutical compositions suitable for delivery to the mucosa of the respiratory tract.

The therapeutical use of inhibitors of neuraminidase is broadly described in the literature. As reviewed by Burch et al. (Lancet Infect Dis. 2009 September; 9(9):537-45) the overall benefit of neuraminidase inhibitors is primarily seen in a reduction of the average time period lapsed between the occurrence of the first symptoms of infection and the beginning of symptom alleviation in influenza virus-infected adults. For example, the administration of the antiviral drug zanamavir to infected patients of the non-risk adults group, i.e. to adults not belonging to the YOPI group (YOPI=young, old, pregnant, immunocompromised), may reduce the median value for the time interval lapsed until achievement of detectable symptom alleviation by 0.57 days, while the administration of an alternative drug oseitamivir achieves a reduction by 0.55 days. When administered to individuals of the YOPI-group, i.e. people at increased risk of falling ill upon viral infection, the time median value until detection of symptom alleviation is reported to be reduced by 0.98 days when using zanamivir, and by 0.74 days when using oseltamivir. These data suggest that there may be room as well as a need for improved therapeutic strategies.

According to the prescription information contained in commercially available packages of TAMIFLU® (oseltamivir) and RELENZA® (zanamivir) the active ingredients are indicated for the treatment of uncomplicated acute illness due to influenza virus infection in patients who have been symptomatic for no more than 2 days. Thus, for patients having been symptomatic for more than 2 days no therapeutically effective treatment seems to be currently available.

Also, the increasing frequency of viral resistance towards the presently available FDA-approved anti-influenza virus drugs further emphasizes the urgent need for improved antiviral compounds that could be used to combat future influenza virus epidemics or pandemics (Ludwig S.; J Antimicrob Chemother. 2009 July; 64(1):1-4.)

DESCRIPTION OF THE INVENTION

It is therefore an object of the present invention laid down in the claims to provide for an efficient strategy for the prophylactic or therapeutic treatment of influenza virus infection overcoming the above-mentioned drawbacks and preferably even relieving infection-related symptoms in patients having been symptomatic for 2 days or more.

It has surprisingly been found that the use of iota- and/or kappa-carrageenan in combination with a neuraminidase inhibitor such as oseltamivir (TAMIFLU®) or zanamivir (RELENZA®), exhibits synergistic therapeutic effects, i.e. a substantially improved curative or symptom-alleviating effect in the course of influenza virus infection as compared to the corresponding effect of each of the aforementioned compounds when administered alone.

Further, it has surprisingly been found that the combination of iota- and/or kappa-carrageenan with a neuraminidase inhibitor provides additional benefit to patients. Contrary to previous observations it was determined by a validated quantitative real time-PCR procedure that more than half of the individuals (24 out of 42 children) diagnosed for an upper respiratory infection were infected by an influenza A or B virus and in addition by at least one other respiratory virus. Thus, it may be concluded that a treatment targeting only one virus will be of limited success. In contrast, a combined therapy with iota- and/or kappa-carrageenan together with a neuraminidase inhibitor is highly likely not only to be effective against influenza virus but also against respiratory viruses that cause co-infections, the respiratory virus preferably being selected from the group consisting of rhinovirus, coronavirus, and paramyxovirus.

Thus, in a first embodiment the present invention relates to iota- and/or kappa-carrageenan together with a neuraminidase inhibitor for use as a medicament in a combined prophylactic or therapeutic treatment of a symptom, condition or disease caused by or associated with an infection by an influenza virus, optionally including such symptom, condition or disease caused by a co-infection of at least one other respiratory virus, typically selected from the group consisting of rhinovirus, coronavirus, and paramyxovirus.

In a further aspect the invention relates to iota- and/or kappa-carrageenan together with a neuraminidase inhibitor for such a use, wherein the influenza virus is influenza virus A or B.

In a further aspect the invention relates to iota- and/or kappa-carrageenan together with a neuraminidase inhibitor for the aforementioned use, wherein the paramyxovirus is respiratory syncytial virus, metapneumovirus or parainfluenzavirus.

The neuraminidase inhibitor may be selected from but is not limited to the group consisting of zanamivir, oseltamivir, peramivir and laninamivir.

In a further aspect the invention relates to iota- and/or kappa-carrageenan together with a neuraminidase inhibitor for such a use, wherein the neuraminidase inhibitor is zanamivir or oseltamivir.

TAMIFLU® as available on the market comprises oseltamivir phosphate, which is a pro-drug of the active metabolite oseltamivir carboxylate, and is specifically adapted for oral administration. Where intranasal administration is intended according to the present invention the active form oseltamivir carboxylate may be used instead of the phosphate pro-drug form.

Thus, the term "oseltamivir" as used herein refers to either oseltamivir carboxylate or oseltamivir phosphate, unless explicitly stated otherwise or unless a different meaning is derivable from the disclosure.

The condition or disease to be prevented, treated or alleviated is selected primarily from the group consisting of acute bronchitis, chronic bronchitis, rhinitis, sinusitis, croup, acute bronchiolitis, pharyngitis, tonsillitis, laryngitis, tracheitis, asthma and pneumonia while said symptom to be prevented, treated or alleviated is selected from the group consisting of fever, pain, dizziness, shivering, sweating, and dehydration.

By experimental data in a mouse model it was shown that the synergistic effect of iota- and/or kappa-carrageenan with neuraminidase-inhibitors provides an increased therapeutic window opening beyond the currently available therapeutic window of just 48 hours after occurrence of first symptoms of infection, as reported in connection with the administration of the aforementioned commercially available neuraminidase inhibitor drugs. The present invention for the first time allows for a successful treatment of diseased patients even after a period of more than 2 days from the first occurrence of symptoms.

Accordingly, the invention also relates to a combined use of iota- and/or kappa-carrageenan and a neuraminidase inhibitor for the aforementioned purposes, wherein medication is started 24 hours or more post infection.

In a further aspect the invention relates to iota- and/or kappa-carrageenan in combination with a neuraminidase inhibitor for the aforementioned use, wherein administration of medicaments containing the carrageenan component and the neuraminidase inhibitor component either separately or mixed together in a single pharmaceutical composition is started 48 hours or more post infection.

In another embodiment the present invention relates to iota- and/or kappa-carrageenan together with a neuraminidase inhibitor for use in the manufacture of a pharmaceutical composition or a kit of parts suitable for a combined prophylactic or therapeutic treatment of a symptom, condition or disease caused by or associated with an infection by an influenza virus.

In yet another embodiment the present invention relates to a method of prophylactic or therapeutic intervention or treatment of a symptom, condition or disease caused by or associated with either or both of an infection by an influenza virus and a co-infection by at least one other respiratory virus, the respiratory virus typically selected from the group consisting of rhinovirus, coronavirus, and paramyxovirus, the method comprising administering to an individual at risk of or suffering from a said infection or co-infection or both an anti-viral effective amount of iota- and/or kappa-carrageenan in combination with an anti-viral effective amount of a neuraminidase inhibitor.

In a further aspect the invention relates to such a method, wherein the neuraminidase inhibitor is selected from the group consisting of zanamivir, oseltamivir, peramivir and laninamivir.

In a further aspect the invention relates to such a method, wherein the administration of iota- and/or kappa-carrageenan in combination with the neuraminidase inhibitor is started 24 hours or more post infection.

In a further aspect the invention relates to such a method, wherein the administration of iota- and/or kappa-carrageenan in combination with the neuraminidase inhibitor is started 48 hours or more post infection.

Pharmaceutical dosage units of the combined therapy of the present invention may be administered by any suitable route, which includes but is not limited to oral, inhalative or intranasal administration or to any combination of oral, inhalative and intranasal administration.

In a further aspect the invention relates to such a method, wherein the administration is done by oral, inhalative or intranasal administration, or any combination thereof. In a further aspect the invention relates to such a method, wherein the neuraminidase inhibitor is provided as a liquid pharmaceutical composition and is administered orally, while the carrageenan compound us provided as a liquid solution and is administered intranasally, optionally by spraying.

In another aspect the invention relates to a pharmaceutical composition suitable for prophylactic or therapeutic application against influenza virus infection, comprising an antiviral effective amount of iota and/or kappa carrageenan and an antiviral effective amount of a neuraminidase inhibitor.

The absolute bioavailability of the active metabolite of orally administered oseltamivir has been found to be about 80% in the mouse model. The active metabolite is detectable in murine plasma within 30 minutes after administration and reaches maximal concentrations after 3 to 4 hours following administration of the drug. The absolute bioavailability of orally administered zanamivir has been found to be very low, however, i.e. only about 2% on average. After intranasal application or oral inhalation of zanamivir, a median of 10 to 20% of the dose administered was systemically absorbed, with maximum serum concentrations generally being reached within 1 to 2 hours after administration.

Due to a higher viscosity of a liquid solution comprising a neuraminidase inhibitor together with iota and/or kappa carrageenan compared to such a liquid solution without a carrageenan compound the detention time of the neuraminidase inhibitor to the mucosa is increased and thereby the systemic uptake in the body is improved.

Thus, intranasal administration of a liquid solution comprising a neuraminidase inhibitor together with iota and/or kappa carrageenan does not only offer the possibility of direct treatment of an individual with the neuraminidase inhibitor, i.e. zanamivir or the active metabolite of oseltamivir, in the nasal cavity which is the main site of viral replication, but allows also for obtaining the necessary systemic drug levels of the neuraminidase inhibitor by administration of a lower amount of said drug.

In a further aspect the invention relates to such a pharmaceutical composition comprising both of a neuraminidase inhibitor and iota and/or kappa-carrageenan, adapted as a nasal spray.

In the case of zanamivir no oral formulation is available at the moment resulting in poor sales of the medicament that currently needs to be inhaled. The inclusion of an anti-viral effective amount of zanamivir in a nasal spray formulation comprising iota and/or kappa carrageenan results in local and systemic efficacy of zanamivir in combination with the anti-viral effect of iota- and/or kappa-carrageenan and thereby in a dramatic improvement of the anti-influenza therapeutic effect of zanamivir.

In a further aspect the invention relates to such a pharmaceutical composition, wherein said neuraminidase inhibitor is zanamivir.

In a further aspect the invention relates to such a pharmaceutical composition, wherein said neuraminidase inhibitor is oseltamivir, in particular oseltamivir carboxylate.

In another aspect the invention relates to a kit of parts suitable for prophylactic or therapeutic treatment of influenza virus infection, comprising a first container comprising an antiviral effective amount of iota and/or kappa carrageenan together with a pharmaceutically acceptable carrier, and a second container comprising an antiviral effective amount of a neuraminidase inhibitor together with a with a pharmaceutically acceptable carrier, and preferably a package insert containing instructions for a combined use of said antiviral effective components.

Effective dosage amounts of combinations of kappa- and iota-carrageenan with neuraminidase inhibitors in accordance with the present invention may comprise usual pharmaceutical dosage units containing the combination of neuraminidase inhibitor at a dosage typically ranging from 0.01-10 mg/kg/d (oseltamivir) or ranging from 0.01-1 mg/kg/d (zanamivir), and of carrageenan polymer at a dosage of from 0.1-50 µg/kg/d, preferably from 2-35 µg/kg/d and most preferred from 8-25 µg/kg/d.

The polymer doses are supplied intranasally or by inhalation typically of from 100-400 µl per application. For example a combination product containing kappa and iota-carrageenan at a concentration of 2400 µg/ml is applied three times per day by spraying 140 μl in each nostril. This corresponds to a daily dose of 2016 μg/d or approximately 27 μg/kg/d.

The present invention is further illustrated by the following figures and examples without being limited thereto.

BRIEF DESCRIPTION OF THE FIGURES

FIG. 1 shows the effect of a combination treatment with iota-carrageenan and Tamiflu® on the survival of mice infected with influenza virus; antiviral treatment was started 2 days post infection.

Ordinate=survival of mice in percentage; abscissa=days post infection.

open diamonds=negative control (placebo); treated intranasally with 25 μl of 0.5% NaCl solution per nostril, dark squares=treated with iota-carrageenan, dark circles=treated with TAMIFLU®, dark triangles=treated with a combination of iota-carrageenan and TAMIFLU®.

FIG. 2 shows the effect of a combination treatment with iota-carrageenan and Tamiflu® on the weight of mice infected with influenza virus when treatment was started 1 day post infection.

Ordinate=mean weight of mice in gram; abscissa=days post infection.

open circles=negative control (placebo) treated with 25 μl of 0.5 NaCl per nostril; dark squares=treated with iota-carrageenan, dark circles=treated with TAMIFLU®, dark triangles=treated with a combination of iota-carrageenan and TAMIFLU®.

FIG. 3 shows the effect of a combination treatment with iota-carrageenan and oseltamivir on the survival of mice infected with influenza virus; antiviral treatment was started 2 days post infection Ordinate=survival of mice in percentage; abscissa=days post infection.

dark circles=negative control (placebo); treated intranasally with 25 μl of 0.5% NaCl solution per nostril, dark squares=treated with oseltamivir, dark diamonds=treated with iota-carrageenan, dark triangles=treated with a combination of iota-carrageenan and oseltamivir.

FIG. 4 shows the effect of a combination treatment with iota-carrageenan, kappa-carrageenean and zanamivir on the survival of mice infected with influenza virus; antiviral treatment was started 2 days post infection.

Ordinate=survival of mice in percentage; abscissa=days post infection.

dark circles=negative control (placebo), treated intranasally with 25 μl of 0.5% NaCl solution per nostril; dark squares=treated with zanamivir; dark diamonds=treated with a combination of iota-carrageenan and kappa-carrageenan; dark triangles=treated with a combination of iota-carrageenan, kappa-carrageenean and zanamivir.

EXAMPLES

In order that the present invention may be better understood the following examples are set forth. They are not to be construed, however, to limit the invention in any respect.

Example 1: Synergistic Therapeutic Effect of Iota-Carrageenan and TAMIFLU® in Mice with Treatment Starting 48 Hours Post Infection 40 C57B16 mice were infected with a lethal dose (10× $LD_{50}$) of influenza A/PR/8/34 virus by intranasal instillation (i.n.) without anaesthesia. After infection of the nasal cavity the virus spreads in the respiratory tract and finally causes a lethal pneumonia in mice. This model mimics the natural influenza infection in humans via the respiratory tract that sometimes causes severe conditions.

The mice were divided into four groups of 10 mice each. 48 hours post infection the mice were treated twice daily i.n. without anaesthesia, wherein the first group was treated with a placebo (25 μl 0.5% aqueous NaCl-solution per nostril) as a negative control and the second group was treated solely with 25 μl per nostril of a aqueous iota-carrageenan polymer solution at a concentration of 1200 μg/ml. Group three and four were fed with 10 mg/kg/d of TAMIFLU® per os, wherein the third group additionally received the iota-carrageenan polymer intranasally at the above concentration whereas the fourth group received the intranasal placebo treatment in addition to the oral Tamiflu® administration. The treatment without anaesthesia ensures that the carrageenan polymer administered does not reach the lungs and thus allows for measuring the inhibitory effect of the polymer on the spreading of the virus in the respiratory tract. The survival of the animals was determined daily as a surrogate parameter for health. The difference in the number of surviving animals was evaluated using a log-rank test.

As shown in FIG. 1 all mice of the placebo treated group (open diamonds) died within 11 days. The survival of mice was significantly improved when treated either with iota-carrageenan (dark squares, 4/10=4 survivors out of 10) or TAMIFLU® (dark circles, 3/10). However, when the mice were treated with iota-carrageenan in combination with TAMIFLU® (dark triangles) 6 out of 10 animals survived the lethal influenza virus infection.

Given the high predictability of mouse models for the development of anti-influenza drugs this result demonstrates that the therapeutic efficacy of oral TAMIFLU® dosages can be significantly increased when provided in combination with intranasal administration of iota-carrageenan dosages, even in cases where the therapy starts only 48 hours post infection. This is of particular importance since no therapeutic regimen appears to be currently available for such cases.

Example 2: Synergistic Therapeutic Effect of Iota-Carrageenan and TAMIFLU® in Mice with Treatment Starting 24 Hours Post Infection Since it is known for TAMIFLU® (oseltamivir phosphate) that the therapeutic efficacy is best when the treatment is started within 24 hours after the appearance of the first symptoms of infection, it was analysed whether the combined treatment with iota-carrageenan could improve the therapeutic efficacy of TAMIFLU®. Since the treatment with TAMIFLU® already provides a high degree of protection from fatal outbreak of the disease the mean animal weight was used as a surrogate parameter for the estimation of the animals' health. The animal weight was compared using the t-test. The experiment was conducted as described in Example 1 the only difference being that treatment started already 24 hours post infection.

Figure 2:
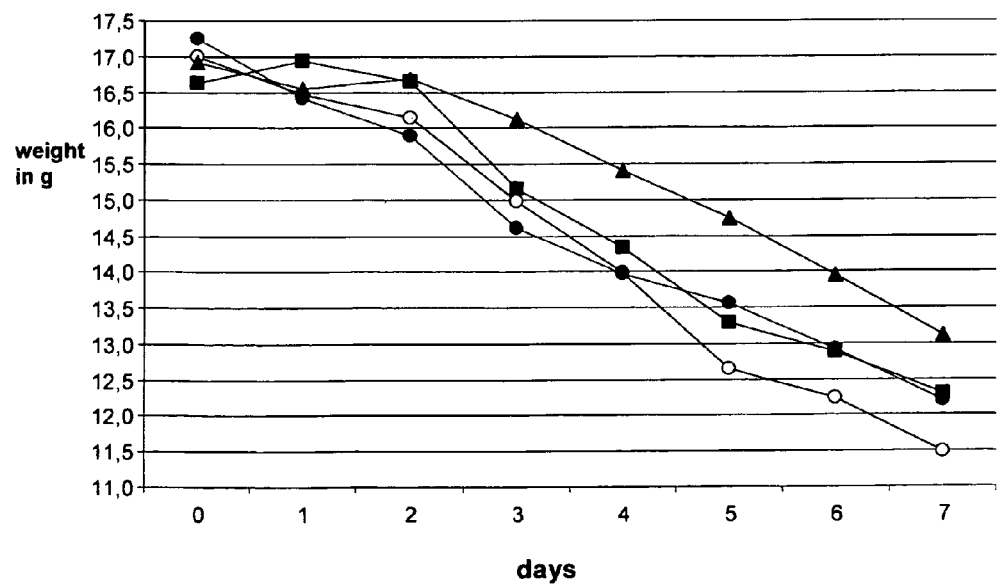

As shown in FIG. 2 all animals encounter a weight loss due to the lethal influenza virus infection. Although treatment with either TAMIFLU® (dark circles) or iota-carrageenan (dark squares) as the sole active ingredient already resulted in a dramatic increase in survival rate (see Example 1), said treatment although started already 24 hours post infection failed to provide a significant benefit with regard to weight loss in the first seven days. In contrast thereto, the combined treatment with TAMIFLU® and iota-carrageenan (dark triangles) resulted in a synergistic effect as determined by a significantly lesser weight loss when compared to placebo treatment (open circles) as can be seen in the figure as from day 3 onwards ($p_{max}$<0,004). In addition, the combination of TAMIFLU® and iota-carrageenan was significantly better when compared with TAMIFLU® alone on days 2, 3 and 4, indicating a therapeutic superiority of the combined treatment over the sole treatment with TAMIFLU® as the only active.

Example 3: Synergistic Therapeutic Effect of Iota-Carrageenan and Oseltamivir in Mice by Treatment Starting 48 Hours Post Infection The infection of the mice was done as described in Example 1. The mice were divided into four groups of 10 mice each. 48 hours post infection the mice were treated twice daily i.n. without anaesthesia, wherein the first group was treated with a placebo (25 µl 0.5% aqueous NaCl-solution per nostril) as a negative control, the second group was treated orally with oseltamivir at a dosage of 5 mg/kg/d, the third group was treated with 25 µl per nostril of an aqueous iota-carrageenan polymer solution at a concentration of 1200 µg/ml, and the fourth group was treated with a combination of iota-carrageenan and oseltamivir twice daily, wherein oseltamivir was administered orally at a dosage of 5 mg/kg/d and the total amount of iota-carrageenan administered intranasally was 100 µl corresponding to an amount of 120 µg per day. The survival of the animals was determined daily as a surrogate parameter for health. The difference in the number of surviving animals was evaluated using a log-rank test.

Figure 3:
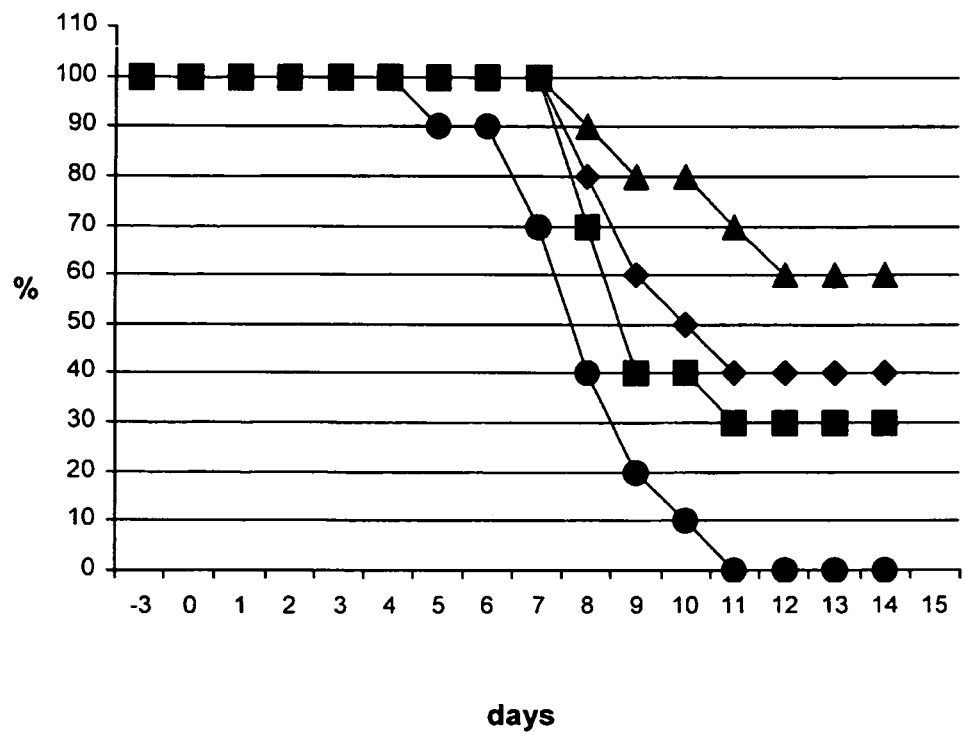

As shown in FIG. 3 the survival of mice was significantly improved when treated by a combination therapy comprising intranasal administration of iota-carrageenan and oral administration of oseltamivir (6/10) as compared to the placebo (0/10), a treatment with oseltamivir alone (3/10) or a treatment with iota-carrageenan alone (4/10). This result demonstrates that a treatment of mice 48 hours post infection with oselatamivir can be significantly improved when combined with intranasal treatment by iota-carrageenan.

Example 4: Synergistic Therapeutic Effect of Iota-Carrageenan, Kappa-Carrageenan and Zanamivir in Mice with Treatment Starting 48 Hours Post Infection The experiment was conducted as described in Example 3 the differences being that intranasally administered zanamivir (0.5 mg/kg/d) was used instead of orally administered oseltamivir, that a combination of iota-carrageenan and kappa-carrageenan was used instead of iota-carrageenan alone (total amount of carrageenan polymer administered intranasally was 100 µl corresponding to an amount of 120 µg per day), the group size was 20 mice per group and the zanamavir concentration in the aqueous solution used was 0.1 mg/ml corresponding to 0.5 mg of active drug per 1 kg body weight (average weight per mouse approx. 20 g).

Figure 4:
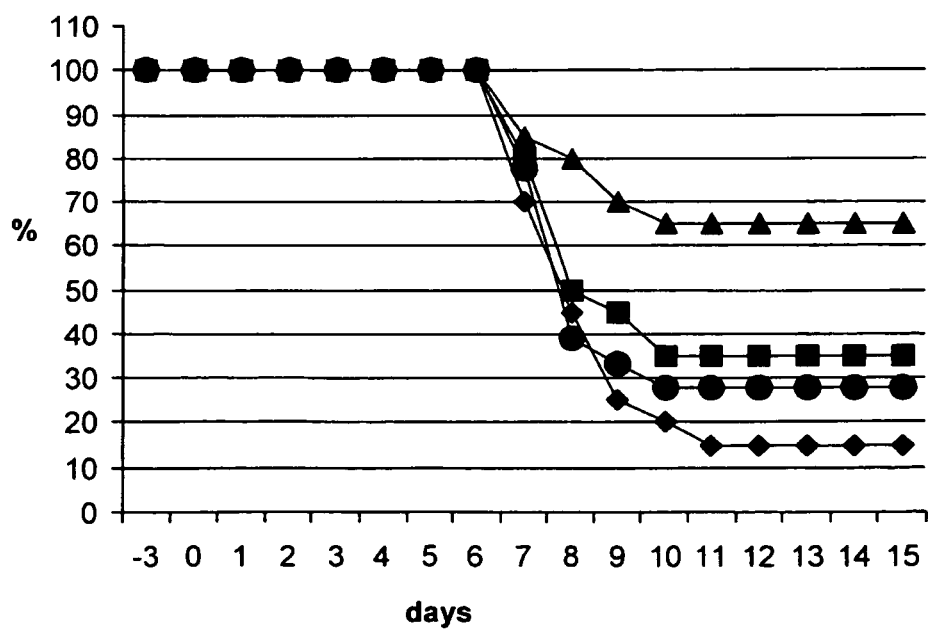

As shown in FIG. 4 the survival of mice was significantly improved when treated with a triple combination of iota-carrageenan, kappa-carrageenan and zanamivir (13/20) when compared to treatment with zanamivir alone (7/20), a combination of iota-carrageenan and kappa-carrageenan (3/20) or the placebo (5/20). This result demonstrates that an otherwise ineffective intranasal treatment of mice with zanamivir can be significantly improved when combined with a mixture of kappa- and iota-carrageenan, suggesting a positive therapeutic outcome even when treatment is started later than 48 hours post infection.

What is claimed is:
1. A pharmaceutical composition for the treatment of a symptom, condition or disease caused by an infection with influenza virus or by a co-infection with influenza virus and at least one other respiratory virus, wherein the condition or disease is at least one selected from the group consisting of acute bronchitis, chronic bronchitis, rhinitis, sinusitis, croup, acute bronchiolitis, pharyngitis, tonsillitis, laryngitis, tracheitis, asthma and pneumonia, and wherein the symptom is selected from the group consisting of fever, pain, dizziness, shivering, sweating, and dehydration, the composition comprising:
   an antiviral effective amount of at least one carrageenan selected from the group consisting of iota carrageenan and kappa carrageenan; and
   an antiviral effective amount of zanamivir as a neuraminidase inhibitor;
   the concentration of the carrageenan being 1.2 mg/ml and the concentration of the zanamivir being 0.1 mg/ml in the composition.
2. The pharmaceutical composition of claim 1, adapted as a nasal spray.
3. The pharmaceutical composition of claim 1, wherein the at least one other respiratory virus is selected from the group consisting of rhinovirus, coronavirus, and paramyxovirus.
4. The pharmaceutical composition of claim 3, wherein the at least one other respiratory virus is selected from the group consisting of respiratory syncytial virus, metapneumovirus, and parainfluenzavirus.
5. A kit of parts comprising the pharmaceutical composition of claim 1, comprising:
   a first container comprising the antiviral effective amount of the at least one carrageenan selected from the group consisting of iota carrageenan and kappa carrageenan together with a pharmaceutcially acceptable carrier;
   a second container comprising the antiviral effective amount of the zanamivir neuraminidase inhibitor together with a pharmaceutcially acceptable carrier; and
   instructions for a combined use of said antiviral effective components.
6. The kit of parts of claim 5, wherein the at least one other respiratory virus is selected from the group consisting of rhinovirus, coronavirus, and paramyxovirus.

7. The kit of parts of claim 6, wherein the at least one other respiratory virus is selected from the group consisting of respiratory syncytial virus, metapneumovirus, and parainfluenzavirus.

* * * * *